(12) United States Patent
Koufaki et al.

(10) Patent No.: US 7,115,657 B2
(45) Date of Patent: Oct. 3, 2006

(54) BIFUNCTIONAL AGENTS POSSESSING ANTIOXIDANT AND ANTIARRHYTHMIC ACTIVITY

(75) Inventors: Maria Koufaki, Athens (GR); Theodora Calogeropoulou, Athens (GR); Alexandros Makriyannis, Boston, MA (US)

(73) Assignee: Uni-Pharma Kleon Tsetis Pharmaceutical Laboratories S.A., (GR)

( * ) Notice: Subject to any disclaimer, the term of this patent is extended or adjusted under 35 U.S.C. 154(b) by 486 days.

(21) Appl. No.: 10/332,464

(22) PCT Filed: Jul. 4, 2001

(86) PCT No.: PCT/GR01/00030

§ 371 (c)(1),
(2), (4) Date: Jan. 9, 2003

(87) PCT Pub. No.: WO02/04438

PCT Pub. Date: Jan. 17, 2002

(65) Prior Publication Data

US 2004/0259763 A1    Dec. 23, 2004

(30) Foreign Application Priority Data

Jul. 12, 2000   (GR) ............................. 20000100231

(51) Int. Cl.
*A61K 31/355*   (2006.01)
*C07D 311/72*   (2006.01)

(52) U.S. Cl. ..................... 514/458; 549/404; 549/405; 549/408

(58) Field of Classification Search ............... 549/404, 549/405, 408; 514/458
See application file for complete search history.

(56) References Cited

FOREIGN PATENT DOCUMENTS

EP        0 293 078        11/1988

OTHER PUBLICATIONS

P. J. Silver et al, "Low Molecular Weight Analogs of Trolox with Potent Antioxidant Activity in Vitro and In Vivo," Chemical Abstracts, vol. 117, No. 1, p. 19, 1992, Columbus, Ohio, US, XP-002163993.

*Primary Examiner*—Taofiq Solola
(74) *Attorney, Agent, or Firm*—Finnegan, Henderson, Farabow, Garrett & Dunner LLP

(57) ABSTRACT

The present invention relates to novel bifunctional agents possessing antioxidant and antiarrhytmic activity, methods for the synthesis of the same and their applications in treating ischemia-reperfusion injury, as well as a variety of disorders related to free radicals and/or arrhythmias. These bifunctional drugs should preferentially segregate in the membrane and produce their antiarrhytmic effects while, at the same time, help in protecting the membrane lipids by scavenging free radicals. The present invention comprises compounds represented by Formula (I), wherein $R_1$, $R_2$, $R_3$, $R_4$, $R_5$ are further defined

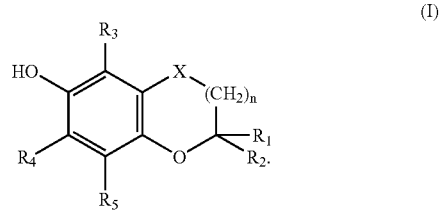

7 Claims, No Drawings

BIFUNCTIONAL AGENTS POSSESSING ANTIOXIDANT AND ANTIARRHYTHMIC ACTIVITY

FIELD OF THE INVENTION

The present invention relates to novel bifunctional agents possessing antioxidant and antiarrhythmic activity, methods for the synthesis of the same and their applications in treating ischemia-reperfusion injury, as well as a variety of disorders related to free radicals and/or arrhythmias.

BACKGROUND OF THE INVENTION

The majority of life threatening ventricular arrhythmias occur in patients suffering from ischemic heart disease. Reperfusion (reoxygenation) of the ischemic heart tissue and administration of antiarrhythmic drugs, follow the case of myocardial infarctions. However the use of antiarrhythmic drugs to suppress arrhythmias and prevent sudden cardiac death has limited success (Woosley R. L. "Antiarrhythmic drugs" *Annu. Rev. Pharmacol. Toxikol.* 1991, 31, 427).

Accumulated evidence suggests that the injury sustained by the heart, following a case of acute myocardial ischemia occurs during reoxygenation. It is believed that the biochemical changes occurring during the ischemic period produce a burst of active oxygen species (AOS) when molecular oxygenation is reintroduced (McCord J. M. "Oxygen-derived free radicals in postischemic tissue injury" *N. Engl. J. Med.* 1985, 312, 159). These oxygen radicals include superoxide ($*O^{2-}$) which is a precursor of several more toxic radicals such as hydroxyl radical ($*OH$). It is postulated that these free radicals react with the phospholipid components of myocardium. Such reactions affect the selective permeability of cell membranes and are related to the development of life threatening ventricular arrhythmias and/or fibrillation. Under normal conditions cells are protected from such reactions by various enzymes and by some small molecules which are normally involved in cellular redox reactions. However, these biochemical processes are inadequate during hypoxic conditions. Treatment with antioxidants such as α-tocopherol has been shown to reduce membrane related alterations resulting from ischemia and reperfusion (Massey K. D., Burton K. P. "α-Tocopherol attenuates myocardial membrane-related alterations resulting from ischemia and reperfusion" *Am. J. Physiol.* 1989, 256, H1192).

Accordingly, it would be advantageous to develop bifunctional agents which will act as antiarrhythmic antioxidants. These bifunctional drugs should preferentially segregate in the membrane and produce their antiarrhythmic effects while, at the same time, help in protecting the membrane lipids by scavenging free radicals.

Thus the pharmacophore backbone of structural analogs of vitamin E and key features responsible for the antiarrhythmic properties of class I or class III antiarrhythmics were combined in one molecular scaffold. Lipophilic features have been incorporated in order to achieve favorable partitioning in the myocardial membranes.

The molecular design also has taken into account all available information on structure activity relationships for optimal antiarrhythmic activity with minimal undesirable effects.

SUMMARY OF THE INVENTION

The present invention comprises compounds represented by Formula I.

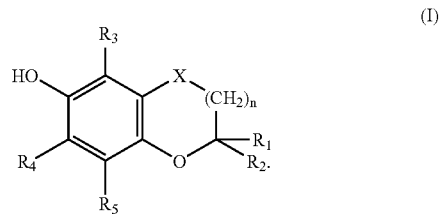

X=$CH_2$, NC(O)$CH_2$NR'R", CHNHC(O)$CH_2$NR'R", NC(O)R''', CHNHC(O)R''', n=1
X=$CH_2$, n=0
$R_1$=H, alkyl, alkenyl, alkynyl, aryl all of which may be optionally substituted
$R_2$=Alkyl, aryl, C(O)NH($CH_2CH_2$)$_m$NR'R", C(O)YC(O)R''', $CH_2$Y(CO)R'''
$CH_2$YC$H_2$R''' with the proviso that when X=$CH_2$, n=1, $R_1$=$R_3$=$R_4$=$R_5$=Me to $R_2$ can not be C(O)NHC$H_2$C$H_2$N(Me)$_2$
$R_3$=Alkyl, C(O)NH($CH_2CH_2$)$_m$NR'R", NHC(O)$CH_2$NR'R", NHC(O)R'''
$R_4$, $R_5$=Lower alkyl
Y=HN($CH_2CH_2$)$_m$NH, NHCH$R_1$NH, HN-cycloalkyl-NH, HN-aryl-NH, heterocyclic diamine, m=1–5
R'; R"=Alkyl
R'''=(methylsulfonyl)amino-N-aryl In accordance with the present invention and as used herein, the following terms, when appearing alone or as part of a moiety, are defined with the following meaning, unless explicitly stated otherwise.

The term "alkyl," as used herein at all occurrences, refers to saturated aliphatic groups including straight chain, branched chain, and cyclic groups, all of which may be optionally substituted. Preferred alkyl groups contain 1 to 16 carbon atoms.

The term "alkenyl," as used herein at all occurrences, refers to unsaturated groups which contain at least one carbon-carbon double bond and includes straight chain, branched chain, and cyclic groups, all of which may be optionally substituted.

Preferable alkenyl groups have 2 to 16 carbon atoms.

The term "alkynyl," as used herein at all occurrences, refers to unsaturated hydrocarbon groups which contain at least one carbon-carbon triple bond and includes straight chain and branched chain groups which may be optionally substituted. Preferred alkynyl groups have two to sixteen carbon atoms.

The term "aryl" refers to aromatic groups which have at least one ring having a conjugated π electron system and includes carbocyclic aryl and biaryl, both of which may be optionally substituted. Preferred aryl groups have 6 to 10 carbon atoms.

The term "optionally substituted" or "substituted," unless otherwise specifically defined herein, refers to groups substituted by one to five substituents, independently selected from lower alkyl (acyclic and cyclic), aryl (carboaryl and heteroaryl), alkenyl, alkynyl, alkoxy, halo, haloalkyl (including trihaloalkyl, e.g. trifluoromethyl), amino, mercapto, alkylthio, alkylsulfinyl, alkylsulfonyl, nitro, alkanoyl, alkanoyloxy, alkanoyloxyalkanoyl, alkoxycarboxy, carbalkoxy, carboxamido, formyl, carboxy, hydroxy, cyano, azido, keto and cyclic ketals thereof, alkanoylamido, heteroaryloxy.

The term "lower" is referred to herein in connection with organic radicals or compounds defines one up to and including six. Such groups may be straight chain, branched chain, or cyclic.

The present invention includes all possible stereoisomers of Formula I and includes not only racemic compounds but also the optically active isomers as well. Some specific compounds of Formula I are listed below, the synthesis of which was performed in accordance with the Example Section set forth below.

N-(3,4-dihydro-6-hydroxy-2,5,7,8-tetramethyl-2H-1-benzopyran-2-carbonyl)-N',N'-diethyl ethylenediamine N-(3,4-dihydro-6-hydroxy-2-hexyl-5,7,8-trimethyl-2H-1-benzopyran-2-carbonyl)-N',N'-diethyl ethylenediamine N-(3,4-dihydro-2-dodecyl-6-hydroxy-5,7,8-trimethyl-2H-1-benzopyran-2-carbonyl)-N',N'-diethyl ethylenediamine N-(3,4-dihydro-6-hydroxy-2,2,7,8-tetramethyl-2H-1-benzopyran-5-carbonyl)-N',N'-diethyl ethylenediamine N-(3,4-dihydro-6-hydroxy-2-hexyl-2,7,8-trimethyl-2H-1-benzopyran-5-carbonyl)-N',N'-diethyl ethylenediamine N-(3,4-dihydro-2-dodecyl-6-hydroxy-2,7,8-trimethyl-2H-1-benzopyran-5-carbonyl)-N',N'-diethyl ethylenediamine N-(3,4-dihydro-6-hydroxy-2,2,7,8-tetramethyl-2H-1-benzopyran-5-yl)-(diethylamino)acetamide N-(3,4-dihydro-2-hexyl-6-hydroxy-2,7,8-trimethyl-2H-1-benzopyran-5-yl)-(diethylamino)acetamide N-(3,4-dihydro-6-hydroxy-2,2,5,7,8-pentamethyl-2H-1-benzopyran-4-yl)-(diethylamino)acetamide N-(3,4-dihydro-2-hexyl-6-hydroxy-2,5,7,8-tetramethyl-2H-1-benzopyran-4-yl)-(diethylamino)acetamide

BRIEF DESCRIPTION OF THE DRAWINGS

Synthesis of any compounds of the Formula (I) not specifically set forth herein can be accomplished by methods analogous those illustrated in Figures (A–D) set forth below as well as the methods described in the Example section.

Compound a (R=Me) was prepared from trolox and N,N-diethylethylenediamine in the presence of CDI (Jacobsen E. J., VanDoornik F. J., Ayer D. E., Belonga K. L., Braughler J. M., Hall E. D., Houser D. J. "2-(Aminoethyl) chromans that inhibit iron-dependent lipid peroxidation and protect against central nervous system trauma and ischemia" J. Med. Chem. 1992, 35, 4464). Compounds b, c containing longer alkyl chains at position 2 of the chroman moiety were synthesized from 6-hydroxychroman-2-carbonitriles 1 (prepared by the methods described by (Janero D. A., Cohen N., Burghardt B., Schaer B. H. "Novel 6-hydroxychroman-2-carbonitrile inhibitors of membrane peroxidative injury" Biochem. Pharmacol. 1990, 40, 551). Alkaline hydrolysis of the nitriles afforded the acids 2 which were in turn converted to the corresponding acid chlorides and subsequently to the 6-hydroxy-chroman-2-amides (Figure A).

6-Methoxy-2-methyl-2-alkylchromans 3 [prepared by condensation of 2,3-dimethylhydroquinone with the appropriate allylalcohol (Mukai K., Kageyama Y., Ishida T., Fukuda K. "Synthesis and kinetic study of antioxidant activity of new tocopherol compounds" J. Org. Chem. 1989, 54, 552) and methylation of the resulting 6-hydroxy-2-methyl-2-alkylchromans] were used as starting materials for the synthesis of the compounds d–h (Figures B, C).

Formylation of 3 (Schuda P. F., Price W. A. "Total synthesis of isoflavones. Friedel-Crafts Acylation reactions with acid sensitive substrates" J. Org. Chem. 1987, 52, 1972) gave the 5-chromanaldehydes 4 which were in turn converted to the corresponding acids 5 by oxidation with sodium chlorite-hydrogen peroxide (Dalcanale E., Montanari F. "Selective oxidation of aldehydes to carboxylic acids with sodium chlorite-hydrogen peroxide" J. Org. Chem. 1986, 51, 567). The acids were than converted to acid chlorides which upon reaction with N,N-diethyl ethylenediamine and deprotection of the methoxy group gave the amides d–f (Figure B).

Nitration of 3 using acetyl nitrate (Ohkawa S., Fukatsu K., Miki S., Hashimoto T., Sakamoto J., Doi T., Nagai Y., Aono T. "5-aminocoumarans: Dual inhibitors of lipid peroxidation and dopamine release with protective effects against central nervous system trauma and ischemia" J. Med. Chem. 1997, 40, 559) followed by reduction of the resulting 5-nitrochroman (Ono A., Hiroi M., Shimazaki K. "Reduction of aromatic nitro-compounds by the sodium borohydride-copper (I) chloride system" Chem. Ind. 1984, 75) afforded the corresponding amines 8 which were acylated using bromoacetylchloride. Reaction of bromoamides 9 with diethylamine (Phillips G. B., Morgan T. K., Nickish K., Lind J. M., Gomez R. P., Wohl R. A., Argentieri T. M., Sullivan M. E. "Synthesis and cardiac electrophysiological activity of aryl-substituted derivatives of the class III antiarrhythmic agent sematilide." Med. Chem. 1990, 33, 627) followed by deprotection of the methoxy group gave the amides g, h (Figure C).

For the synthesis of amides i, j 3,6-dihydroxy-2,4,5-trimethyl acetophenone (11) (Pearce B. C., Parker R. A., Deason M. E., Dischino D. D., Gillepsie E., Qureshi A. A., Vold K., Wright K. J. J. "Inhibitors of cholesterol biosynthesis. 2. Hypocholisteronemic and antioxidant activities of benzofuran and tetrahydronaphthalene analogs of the tocotrienols" J. Med. Chem. 1994, 37, 526) was reacted with the corresponding methyl ketone in the presence of pyrrolidine to give chromanones 12 which were converted to oximes 13 (Phillips G. B., Morgan T. K., Nickish K., Lind J. M., Gomex R. P., Wohl R. A., Argentieri T. M., Sullivan M. E. "Synthesis and cardiac electrophysiological activity of aryl-substituted derivatives of the class III antiarrhythmic agent sematilide." J. Med. Chem. 1990, 33, 627). Reduction using TiCl$_4$/NaBH$_4$ afforded amines 14 (Kano S., Tanaka Y., Sugino E., Hibino S. "Reduction of some functional groups with titanium(IV) chloride/sodium borohydride". Synthesis 1980, 695) which were acylated using bromoacetyl chloride to afford amides 15. Reaction of amides 15 with diethylamine afforded compounds i, j. (Figure D).

The present invention also includes the pharmaceutically acceptable salts of the compounds of Formula I as well as pharmaceutical formulations containing these compounds.

GENERAL PROCEDURES

NMR spectra were recorded on a Bruker AC 300 spectrometer operating at 300 MHz for $^1$H and 75.43 MHz for $^{13}$C. $^1$H NMR spectra are reported in units of δ relative to internal CHCl$_3$ at 7.24 ppm. $^{13}$C NMR shifts are expressed in units of δ relative to CDCl$_3$ at 77.0 ppm. $^{13}$C NMR spectra were proton noise decoupled. All NMR spectra were recorded in CDCl$_3$. Silica gel plates (Merck F254) were used for thin layer chromatography. Chromatographic purification were performed with silica gel (200–400 mesh).

General Procedure for the Preparation of 3,4-dihydro-6-hydroxy-2-alkyl-5,7,8-trialkyl-2H-1-benzopyran-2-carboxylic Acids 4.65 mmol of the appropriate nitrile were added to a solution of 20 mL 85% KOH in ethyleneglycol and the mixture was refluxed overnight. The solvent was then removed in vacuo and the residue dissolved in cold water. The solution was acidified with 2N HCl and extracted with AcOEt. The 3,4-dihydro-6-hydroxy-2-alkyl-5,7,8-trialkyl-2H-1-benzopyran-2-carboxylic acid was recrystallized from AcOEt/pet. ether (40–60).

EXAMPLE 1

3,4-dihydro-2-hexyl-6-hydroxy-5,7,8-trimethyl-2H-1-benzopyran-2-carboxylic Acid

Use of 3,4-dihydro-6-hydroxy-2-hexyl-5,7,8-trimethyl-2H-1-benzopyran-2-carbonitrile as employed above afforded 1.18 g (79.1%) of the desired compound named above: $^1$H NMR δ 4.42 (s, 1H), 2.64–2.57 (m, 2H), 2.33–2.28 (m, 1H), 2.17 (s, 6H), 2.11 (s, 3H), 1.9–1.85 (m, 1H), 1.5–1.25 (m, 10H), 0.86 (t, J=6.3 Hz, 3H); $^{13}$C NMR δ 176.9, 145.7, 144.2, 81.0, 37.0, 31.8, 29.4, 28.8, 23.4, 22.6, 20.4, 14.1, 12.3, 11.9, 11.3; Anal. ($C_{19}H_{28}O_4$) C, H.

EXAMPLE 2

3,4-dihydro-2-dodecyl-6-hydroxy-5,7,8-trimethyl-2H-1-benzopyran-2-carboxylic Acid Use of 3,4-dihydro-6-hydroxy-2-dodecyl-5,7,8-trimethyl-2H-1-benzopyran-2-carbonitrile as employed above afforded 1.39 g (73.8%) of the desired compound named above: $^1$H NMR δ 2.62–2.59 (m, 2H), 2.4–2.2 (m, 1H), 2.18 (s, 1H), 2.18 (s, 3H), 2.09 (s, 3H), 1.91–1.86 (m, 1H), 1.5–1.24 (m, 22H), 0.88 (t, J=6.3 Hz, 3H); Anal. ($C_{25}H_{40}O_4$) C, H.

General Procedure for the Preparation of N(3,4-dihydro-6-hydroxy-2,5,7,8-tetraalkyl-2H-1-benzopyran-2-carbonyl)-N',N'-dialkyl-ethylenediamines 1,1'-carbonyldiimidazole (537 mg, 3.3 mmol) was added to a solution of chroman carboxylic acid (3 mmol) in 15 mL THF. After stirring for 1 h at RT, a solution of N,N, dialkyl ethylenediamine in 12 mL THF was added dropwise. The mixture was allowed to stir for 24 h at RT. The solvent was then evaporated in vacuo and the residue was taken up with ethyl acetate and the organic layer was washed with brine and dried ($Na_2SO_4$).

EXAMPLE 3

N-(3,4-dihydro-6-hydroxy-2,5,7,8-tetramethyl-2H-1-benzopyran-2-carbonyl)-N',N'-diethyl Ethylenediamine Use of trolox (750 mg, 3 mmol) as employed above afforded 0.73 g (70%) of the desired compound named above: $^1$H NMR δ 7.13 (bs, 1H), 3.28–3.18 (m, 2H), 2.59–2.31 (m, 9H), 2.18 (s, 3H), 2.17 (s, 3H), 2.16 (s, 3H), 1.89–1.85 (m, 1H), 1.50 (s, 3H), 0.90 (t, J=7.2 Hz, 6H); $^{13}$C NMR δ 174.3, 145.5, 144.3, 121.9, 121.6, 119.1, 117.6, 78.1, 51.3, 46.4, 36.5, 29.4, 24.4, 20.5, 12.2, 11.9, 11.7, 11.3; Anal. ($C_{20}H_{32}N_2O_3$) C, H, N.

EXAMPLE 4

N-(3,4-dihydro-2-hexyl-6-hydroxy-5,7,8-trimethyl-2H-1-benzopyran-2-carbonyl)-N',N'-diethyl Ethylenediamine Use of 3,4-dihydro-2-hexyl-6-hydroxy-5,7,8-trimethyl-2H-1-benzopyran-2-carboxylic acid as employed above afforded 0.308 g (65.5%) of the desired compound named above: $^1$H NMR δ 7.10 (bs, 1H), 4.5 (bs, 1H), 3.37–3.29 (m, 2H), 2.61–2.49 (m, 6H), 2.29–2.2 (m, 1H), 2.16 (s, 3H), 2.11 (s, 3H), 2.05 (s, 3H), 1.95–1.69 (m, 3H), 1.44–1.23 (m, 10H), 1.0 (t, J=7 Hz, 6H), 0.84 (t, J=6.3 Hz, 3H); $^{13}$C NMR δ 175.3, 146.2, 143.1, 122.5, 121.9, 119.6, 117.2, 80.4, 51.2, 46.9, 37.8, 36.3, 31.4, 29.1, 28.4, 23.1, 22.3, 20.0, 13.8, 12.1, 11.8, 11.7, 11.2

EXAMPLE 5

N-(3,4-dihydro-2-dodecyl-6-hydroxy-5,7,8-trimethyl-2H-1-benzopyran-2-carbonyl)-N',N'-diethyl Ethylenediamine Use of 3,4-dihydro-6-hydroxy-2-dodecyl-5,7,8-trimethyl-2H-1-benzopyran-2-carboxylic acid as employed above afforded 0.323 g (58.4%) of the desired compound named above: $^1$H NMR δ 7.15 (bs, 1H), 4.6 (bs, 1H), 3.36–3.34 (m, 2H), 2.61–2.43 (m, 6H), 2.29–2.22 (m, 1H), 2.17 (s, 3H), 2.13 (s, 3H), 2.05 (s, 3H), 2.01–1.73 (m 3), 1.44–1.23 (m, 22H), 1.01 (t, J=7.1 Hz, 6H), 0.87 (t, J=6.1 Hz, 3H); $^{13}$C NMR δ 175.7, 146.1, 143.3, 122.4, 121.9, 119.6, 117.5, 80.7, 50.0, 47.6, 47.4, 36.6, 34.8, 31.8, 29.5, 29.3, 29.2, 28.4, 23.3, 22.5, 20.1, 13.9, 12.4, 11.9, 11.5

General Procedure for the Preparation of 3,4-dihydro-6-methoxy-2,2,7,8-tetraalkyl-2H-1-benzopyran-5-carboxaldehydes To a solution of the appropriate 3,4-dihydro-6-methoxy-2,2,7,8-tetraalkyl-2H-1-benzopyran (5.45 mmol) in 4 mL $CH_2Cl_2$ was added α,α-chloromethyl methyl ether (1.2 mL, 14.5 mmol). The mixture was cooled to 0° C. and a solution of $TiCl_4$ (0.8 mL, 7.8 mmol) in 4 mL $CH_2Cl_2$ was added dropwise. The resulting mixture was stirred at RT for 2 h, poured into ice, extracted with $CH_2Cl_2$ and the organic layer was washed with sat. aqu. $NaHCO_3$, brine and dried ($Na_2SO_4$).

EXAMPLE 6

3,4-dihydro-6-methoxy-2,2,7,8-tetramethyl-2H-1-benzopyran-5-carboxaldehyde

Use of 3,4-dihydro-6-methoxy-2,2,7,8-tetramethyl-2H-1-benzopyran as employed above afforded 1.35 g (100%) of the desired compound named above: $^1$H NMR δ 10.49 (s, 1H), 3.76 (s, 3H), 3.09 (t, J=6.5 Hz, 2H), 2.2 (s, 3H), 2.16 (s, 3H), 1.73 (t, J=6.2 Hz, 2H), 1.29 (s, 6H)

EXAMPLE 7

3,4-dihydro-2-hexyl-6-methoxy-2,7,8-trimethyl-2H-1-benzopyran-5-carboxaldehyde

Use of 3,4-dihydro-2-hexyl-6-methoxy-2,7,8-trimethyl-2H-1-benzopyran as employed above afforded 1.56 g (90%) of the desired compound named above: $^1$H NMR δ 10.47 (s, 1H), 3.74 (s, 3H), 3.05 (t, J=6.4 Hz, 2H), 2.19 (s, 3H), 2.15 (s, 3H), 1.8–1.6 (m, 2H), 1.55–1.51 (m, 2H), 1.36–1.25 (m, 8H), 1.22 (s, 3H), 0.85 (t, J=6.6 Hz, 3H); $^{13}$C NMR δ 193.0, 156.5, 148.0, 134.4, 128.8, 124.0, 120.1, 75.6, 63.5, 39.5, 31.8, 30.8, 29.8, 23.8, 23.5, 22.6, 21.1, 14.0, 13.0, 11.9; Anal. ($C_{20}H_{30}O_3$) C, H.

EXAMPLE 8

3,4-dihydro-2-dodecyl-6-methoxy-2,7,8-trimethyl-2H-1-benzopyran-5-carboxaldehyde Use of 3,4-dihydro-2-dodecyl-6-methoxy-2,7,8-trimethyl-2H-1-benzopyran as employed above afforded 2.19 g (100%) of the desired compound named above: $^1$H NMR δ 10.48 (s, 1H), 3.75 (s, 3H), 3.06 (t, J=7 Hz, 2H), 2.20 (s, 3H), 2.16 (s, 3H), 1.76–1.55 (m, 2H), 1.54–1.49 (m, 2H), 1.40–1.25 (m, 20H), 1.23 (s, 3H), 0.86 (t, J=6.7 Hz, 3H); Anal. ($C_{26}H_{42}O_3$) C,H.

General Procedure for the Preparation of 3,4-dihydro-6-methoxy-2,2,7,8-tetraalkyl-2H-1-benzopyran-5-carboxylic Acids A solution of $NaClO_2$ 80% (800 mg, 7 mmol) in 7 mL $H_2O$ was added dropwise to a stirred mixture of the appropriate 3,4-dihydro-6-methoxy-2,2,7,8-tetraalkyl-2H-1-benzopyrancarboxaldehyde (4 mmol), $NaH_2PO_4 \cdot H_2O$ (160 mg, 1.3 mmol), 0.5 mL $H_2O_2$ 35% and 2 mL $H_2O$ and 10 mL MeCN at 10° C. The mixture was stirred at RT overnight. Subsequently, 50 mg of $Na_2SO_3$ were added to destroy HOCl and excess $H_2O_2$ and the aqueous phase was extracted with $CH_2Cl_2$. The organic phase was washed with 2N NaOH. Acidification of the aqueous phase (conc. HCl) and extraction with $CH_2Cl_2$ afforded the title compounds.

EXAMPLE 9

3,4-dihydro-6-methoxy-2,2,7,8-tetramethyl-2H-1-benzopyran-5-carboxylic Acid

Use of 3,4-dihydro-6-methoxy-2,2,7,8-tetramethyl-2H-1-benzopyran-5-carboxaldehyde as employed above afforded 0.760 g (72%) of the desired compound named above: $^1$H NMR δ 11.0 (bs, 1H), 3.77 (s, 3H), 2.93 (t, J=6.7 Hz, 2H), 2.19 (s, 3H), 2.13 (s, 3H), 1.76 (t, J=6.7 Hz, 2H), 1.31 (s, 6H); Anal. ($C_{15}H_{20}O_4$) C,H.

EXAMPLE 10

3,4-dihydro-2-hexyl-6-methoxy-2,7,8-trimethyl-2H-1-benzopyran-5-carboxylic Acid

Use of 3,4-dihydro-2-hexyl-6-methoxy-2,7,8-trimethyl-2H-1-benzopyran-5-carboxaldehyde as employed above afforded 1.24 g (93%) of the desired compound named above: $^1$H NMR δ 3.67 (s, 3H), 2.8–2.7 (m, 2H), 2.12 (s, 3H), 2.06 (s, 3H), 1.6–1.4 (m, 4H), 1.4–1.25 (m, 8H), 1.17 (s, 3H), 0.85 (t, J=6.5 Hz, 3H)

EXAMPLE 11

3,4-dihydro-2-dodecyl-6-methoxy-2,7,8-trimethyl-2H-1-benzopyran-5-carboxylic Acid Use of 3,4-dihydro-2-dodecyl-6-methoxy-2,7,8-trimethyl-2H-1-benzopyran-5-carboxaldehyde as employed above afforded 1.60 g (96%) of the desired compound named above: $^1$H NMR δ 3.76 (s, 3H), 2.95 (t, J=6.6 Hz, 2H), 2.19 (s, 3H), 2.13 (s, 3H), 1.74–1.37 (m, 4H), 1.35–1.24 (m, 20H), 1.23 (s, 3H), 0.87 (t, J=6.2 Hz, 3H)

General Procedure for the Preparation of N-(3,4-dihydro-6-methoxy-2,2,7,8-tetraalkyl-2H-1-benzopyran-5-carbonyl-N',N'-dialkyl Ethylene Diamines p To a solution of the appropriate 3,4-dihydro-6-methoxy-2,2,7,8-tetraalkyl-2H-1-benzopyran-5-carboxylic acid (1.9 mmol) in 5 mL benzene was added $SOCl_2$ (0.6 mL, 7.5 mmol) and the mixture was refluxed for 2 h. The solvent and the excess thionyl chloride was removed in vacuo. The residue was then diluted with 7mLTHF, N,N-dialkylethylenediamine was added and the mixture was stirred overnight at RT. The solvent was then evaporated, the residue was taken up with AcOEt and the organic layer was washed with brine. The crude product was purified by flash column chromatography ($CH_2Cl_2$/MeOH)

EXAMPLE 12

N-(3,4-dihydro-6-methoxy-2,2,7,8-tetramethyl-2H-1-benzopyran-5-carbonyl)-N',N'-diethyl Ethylenediamine Use of 3,4-dihydro-6-methoxy-2,2,7,8-tetramethyl-2H-1-benzopyran-5-carboxylic acid as employed above afforded 0.52 g (74.5%) of the desired compound named above: $^1$H NMR δ 6.67 (bs, 1H), 3.67 (s, 3H), 3.62.14 3.56 (m, 2H), 2.73 (t, J=6.4 Hz, 2H), 2.71–2.63 (m, 6H), 2.15 (s, 3H), 2.09 (s, 3H) 1.72 (t, J=6.7 Hz, 2H), 1.3 (s, 6H), 1.09 (t, J=7.2 Hz, 6H); Anal. ($C_{21}H_{34}N_2O_3$) .0.5$H_2O$ C,H,N.

EXAMPLE 13

N-(3,4-dihydro-2-hexyl-6-methoxy-2,7,8-trimethyl-2H-1-benzopyran-5-carbonyl)-N',N'-diethyl Ethylenediamine Use of 3,4-dihydro-2-hexyl-6-methoxy-2,7,8-trimethyl-2H-1-benzopyran-5-carboxylic acid as employed above afforded 0.68 g (82.5%) of the desired compound named above: $^1$H NMR δ 6.8 (bs, 1H), 3.63 (s, 3H), 3.61–3.57 (m, 2H), 2.81 (t, J=6 Hz, 2H), 2.72 (q, 6H), 2.11 (s, 3H), 2.06 (s, 3H), 1.8–1.6 (m, 2H), 1.6–1.24 (m, 10H), 1.21 (s, 3H), 1.11 (t, J=7.2 Hz, 6H), 0.84 (t, J=6.7 Hz, 3H); $^{13}$C NMR δ 168.3, 148.0, 147.5, 128.5, 127.4, 127.3, 116.1, 75.6, 62.1, 51.6, 46.9, 39.8, 36.4, 31.8, 30.8, 29.7, 24.1, 23.5, 22.5, 20.0, 14.0, 12.3, 12.1, 10.6; Anal. ($C_{26}H_{44}N_2O_3$) .1.5$H_2O$ C,H,N.

EXAMPLE 14

N-(3,4-dihydro-2-dodecyl-6-methoxy-2,7,8-trimethyl-2H-1-benzopyran-5-carbonyl)-N',N'-diethyl Ethylenediamine Use of 3,4-dihydro-6-methoxy-2-dodecyl-2,7,8-trimethyl-2H-1-benzopyran-5-carboxylic acid as employed above afforded 0.83 g (85%) of the desired compound named above: $^1$H NMR δ 6.6 (bs, 1H), 3.67 (s, 3H), 3.63–3.54 (m, 2H), 2.77–2.6 (m, 8H), 2.15 (s, 3H), 2.09 (s, 3H), 1.75–1.65 (m, 2H), 1.6–1.24 (m, 22H), 1.23 (s, 3H), 1.06 (t, J=7 Hz, 6H), 0.84 (t, J=6.2 Hz, 3H) Anal. ($C_{32}H_{56}N_2O_3$) C,H,N.

General Procedure for the Preparation of of N-(3,4-dihydro-6-hydroxy-2,2,7,8-tetraalkyl-2H-1-benzopyran-5-carbonyl)-N',N'-dialkylethylenediamines To an ice-cooled slurry of NaH (240 mg, 10 mmol) in 5 mL DMF was added EtSH (0.9 mL, 12 mmol) and the mixture was stirred for 15 min at 0° C. A solution of the appropriate N-(3,4-dihydro-6-methoxy-2,2,7,8-tetraalkyl-2H-1-benzopyran-5-carbonyl)-N',N'-dialkyl ethylene diamine (1.24 mmol) in 10 mL DMF was added and the mixture was stirred at 90° C. overnight. The mixture was then poured into $H_2O$ and extracted with AcOEt. The organic layer was washed with brine, dried ($Na_2SO_4$) and the solvent was removed in vacuo. Purification by column chromatography ($CH_2Cl_2$/MeOH 95:5) gave the title compounds.

EXAMPLE 15

N-(3,4-dihydro-6-hydroxy-2,2,7,8-tetramethyl-2H-1-benzopyran-5-carbonyl)-N',N'-diethyl Ethylenediamine Use of N-(3,4-dihydro-6-methoxy-2,2,7,8-tetramethyl-2H-1-benzopyran-5-carbonyl)-N',N'-diethyl ethylenediamine as employed above afforded 0.42 g (97%) of the desired compound named above: $^1$H NMR δ 6.8 (bs, 1H), 3.48 (bs, 1H), 2.82 (t, J=6.5 Hz, 2H), 2.64–2.52 (m, 6H), 2.12 (s, 3H), 2.09 (s, 3H), 1.68 (t, J=6.5 Hz, 2H), 1.28 (s, 6H), 1.0 (t, J=7.1 Hz, 6H); $^{13}$C NMR δ 170.0, 149.6, 124.1, 114.0, 72.7, 51.1, 46.1, 36.9, 32.0, 26.8, 22.4, 12.4, 11.9, 11.1; Anal. ($C_{20}H_{32}N_2O_3$) .$H_2O$ C,H,N.

EXAMPLE 16

N-(3,4-dihydro-2-hexyl-6-hydroxy-2,7,8-trimethyl-2H-1-benzopyran-5-carbonyl)-N',N'-diethyl Ethylenediamine Use of N-(3,4-dihydro-2-hexyl-6-methoxy-2,7,8-trimethyl-2H-1-benzopyran-5-carbonyl)-N',N'-diethyl ethylenediamine as employed above afforded 0.48 g (93%) of the desired compound named above: $^1$H NMR δ 6.74 (bs, 1H), 3.52 (bs, 2H), 2.84 (t, J=6 Hz, 2H), 2.66–2.56 (m, 6H), 2.16 (s, 3H), 2.12 (s, 3H), 1.8–1.6 (m, 2H), 1.6–1.28 (m, 10H), 1.25 (s, 3H), 1.01 (t, J=7 Hz, 6H), 0.87 (t, J=6.2 Hz, 3H); $^{13}$C NMR δ 170.1, 150.1, 144.5, 130.2, 124.2, 114.6, 114.1, 74.8, 51.0, 46.1, 39.8, 36.9, 31.9, 31.3, 29.8, 24.1, 23.6, 22.6, 22.3, 14.1, 12.5, 11.9, 11.3; Anal. ($C_{25}H_{42}N_2O_3$) .0.5$H_2O$ C,H,N.

EXAMPLE 17

N-(3,4-dihydro-2-dodecyl-6-hydroxy-2,7,8-trimethyl-2H-1-benzopyran-5-carbonyl)-N',N'-diethyl Ethylenediamine Use of N-(3,4-dihydro-2-dodecyl-6-methoxy-2,7,8-trimethyl-2H-1-benzopyran-5-carbonyl)-N',N'-diethyl ethylenediamine as employed above afforded 0.60 g (97%) of the desired compound named above: $^1$H NMR δ 7.1 (bs, 1H), 3.56 (bs, 2H), 2.88 (t, J=6 Hz, 2H), 2.69–2.60 (m, 6H), 2.16 (s, 3H), 2.12 (s, 3H), 1.75–1.56 (m, 4H), 1.25 (m, 20H), 1.23 (s, 3H), 1.03 (t, J=7.1 Ha, 6H), 0.87 (t, J=6.3 Hz, 3H); $^{13}$C NMR δ 170.1, 149.9, 144.5, 130.1, 124.2, 114.8, 114.1, 74.7, 51.0, 46.1, 39.8, 36.7, 31.8, 31.3, 29.6, 29.3, 24.0, 23.6, 22.6, 22.2, 14.0, 12.4, 11.9, 10.9; Anal. ($C_{31}H_{54}N_2O_3$) C,H,N.

General Procedure for the Preparation of 3,4-dihydro-6-methoxy-5-nitro-2,2,7,8-tetraalkyl-2H-1-benzopyrans 1.8 mL of acetyl nitrate (prepared from 0.4 mL $HNO_3$ 70% and 1.4 mL $Ac_2O$ at 0° C.) were added to a solution of the appropriate 3,4-dihydro-6-methoxy-2,2,7,8-tetraalkyl-2H-1-benzopyran (1.6 mmol) in 2 mL $Ac_2O$ and 2 mL AcOH at 0° C. The mixture was stirred at 0° C. for 1 h and then poured into ice-water. The aqueous mixture was extracted with AcOEt and the organic layer was washed with sat. aqu. $NaHCO_3$, brine and dried. The title compounds were purified by column chromatography (pet. ether/AcOEt 9:1)

EXAMPLE 18

3,4-dihydro-6-methoxy-5-nitro-2,2,7,8-tetramethyl-2H-1-benzopyran

Use of 3,4-dihydro-6-methoxy-2,2,7,8-tetramethyl-2H-1-benzopyran as employed above afforded 0.40 g (94.8%) of the desired compound named above $^1$H NMR δ 3.75 (s, 3H), 2.65 (t, J=6.6 Hz, 2H), 2.19 (s, 3H), 2.11 (s, 3H), 1.75 (t, J=6.8 Hz, 2H), 1.32 (s, 6H) $^{13}$C NMR δ 147.9, 143.5, 130.0, 128.0, 74.3, 62.7, 31.6, 26.9, 26.7, 18.4, 12.6, 12.2 Anal. ($C_{14}H_{19}NO_4$) C,H,N.

EXAMPLE 19

3,4-dihydro-6-methoxy-5-nitro-2-hexyl-2,7,8-trimethyl-2H-1-benzopyran

Use of 3,4-dihydro-6-methoxy-2-hexyl-2,7,8-trimethyl-2H-1-benzopyran as employed above afforded 0.40 g (74.5%) of the desired compound named above $^1$H NMR δ 3.75 (s, 3H), 2.63 (t, J=6.7 Hz, 2H), 2.19 (s, 3H), 2.11 (s, 3H), 1.76–1.36 (m, 4H), 1.36–1.28 (m, 8H), 1.25 (s, 3H), 0.85 (t, J=6.9 Hz, 3H) Anal. ($C_{19}H_{29}NO_4$) C,H,N.

General Procedure for the Preparation of 5-amino-3,4-dihydro-6-methoxy-2,2,7,8-tetraalkyl-2H-1-benzopyrans To a solution of 3,4-dihydro-6-methoxy-5-nitro-2,2,7,8-tetraalkyl-2H-1-benzopyran (1.4 mmol) in 15 mL EtOH were sequentially added CuCl (620 mg, 6.3 mmol) and $NaBH_4$ (480 mg, 12.6 mmol) at 0° C. The mixture was refluxed for 1 h, then cooled to RT, basified ($NaHCO_3$), filtered and washed with $CH_2Cl_2$. The filtrate was evaporated and the residue extracted with $CH_2Cl_2$ and washed with brine. The organic layer was dried and the solvent was removed in vacuo.

EXAMPLE 20

5-amino-3,4-dihydro-6-methoxy-2,2,7,8-tetramethyl-2H-1-benzopyran

Use of 3,4-dihydro-6-methoxy-5-nitro-2,2,7,8-tetramethyl-2H-1-benzopyran as employed above afforded 0.27 g (82.3%) of the desired compound named above $^1$H NMR δ 3.69 (s, 3H), 3.58 (bs, 2H), 2.49 (t, J=6.8 Hz, 2H), 2.18 (s, 3H), 2.05 (s, 3H), 1.82 (t, J=6.7 Hz, 2H), 1.31 (s, 6H). $^{13}$C NMR δ 148.0, 138.7, 134.6, 127.6, 114.3, 104.7, 72.8, 59.7, 32.4, 26.7, 18.5, 12.3, 11.1

EXAMPLE 21

5-amino-2-hexyl-3,4-dihydro-6-methoxy-2,7,8-trimethyl-2H-1-benzopyran

Use of 3,4-dihydro-2-hexyl-6-methoxy-5-nitro-2,7,8-trimethyl-2H-1-benzopyran as employed above afforded 0.39 g (91.6%) of the desired compound named above $^1$H NMR δ 3.67 (s, 3H), 3.55 (bs, 2H), 2.46 (t, J=6.8 Hz, 2H), 2.15 (s, 3H), 2.03 (s, 3H), 1.9–1.65 (m, 2H), 1.55–1.5 (m, 2H), 1.5–1.27 (m, 8H), 1.22 (s, 3H), 0.87 (t, J=6.6 Hz, 3H) $^{13}$C NMR δ 147.8, 139.0, 134.5, 127.5, 114.4, 105.0, 74.8, 59.4, 39.6, 31.8, 30.8, 29.8, 23.8, 23.6, 22.6, 18.2, 14.1, 12.3, 11.1

General Procedure for the Preparation of N-(3,4-dihydro-6-methoxy-2,2,7,8-tetraalkyl-2H-1-benzopyran-5-yl)-bromoacetamides To a solution of 5-amino-3,4-dihydro-6-methoxy-2,2,7,8-tetraalkyl-2H-1-benzopyran (1.28 mmol) in 8 mL THF were added 1 mL $BrCH_2COCl$ and triethylamine at 0° C. After been stirred at RT for 1 h the mixture was poured into $H_2O$ and extracted with AcOEt. The organic layer was washed with sat. aqu. $NaHCO_3$, brine and dried.

EXAMPLE 22

N-(3,4-dihydro-6-methoxy-2,2,7,8-tetramethyl-2H-1-benzopyran-5-yl)-bromoacetamide Use of 5-amino-3,4-dihydro-6-methoxy-2,2,7,8-tetramethyl-2H-1-benzopyran as employed above afforded 0.43 g (94.9%) of the desired compound named above $^1$H NMR δ 7.88 (bs, 1H), 4.05 (s, 2H), 3.63 (s, 3H), 2.58 (t, J=6.6 Hz, 2H), 2.17 (s, 3H), 2.09 (s, 3H), 1.72 (t, J=6.7 Hz, 2H), 1.31 (s, 6H) $^{13}$C NMR δ 164.4, 148.0, 128.3, 125.2, 116.5, 73.7, 61.1, 32.3, 29.0, 26.9, 19.4, 12.4, 12.0

EXAMPLE 23

N-(3,4-dihydro-2-hexyl-6-methoxy-2,7,8-trimethyl-2H-1-benzopyran-5-yl)-bromoacetamide Use of 5-amino-3,4-dihydro-6-methoxy-2-hexyl-2,7,8-trimethyl-2H-1-benzopyran as employed above afforded 0.50 g (92%) of the desired compound named above $^1$H NMR δ 7.9 (bs, 1H), 4.04 (s, 2H), 3.63 (s, 3H), 2.56 (t, J=6.5 Hz, 2H), 2.17 (s, 3H), 2.09 (s, 3H), 1.8–1.65 (m, 2H), 1.65–1.5 (m, 2H), 1.48–1.27 (m, 8H), 1.23 (s, 3H), 0.86 (t, J=6.7 Hz, 3H) $^{13}$C NMR δ 164.4, 148.3, 145.7, 128.2, 125.2, 124.5, 116.8, 75.7, 61.0, 53.4, 40.0, 31.8, 30.7, 29.8, 29.0, 23.9, 23.6, 22.6, 19.0, 14.1, 12.4, 12.0

General Procedure for the Preparation of N-(3,4-dihydro-6-methoxy-2,2,7,8-tetraalkyl-2H-1-benzopyran-5-yl)-(dialkylamino)acetamides To a solution N-[3,4-dihydro-6-methoxy-2,2,7,8-tetraalkyl-2H-1-benzopyran-yl]-bromoacetamide (1.18 mmol) in 7 mL toluene at 0° C. was added 3 mmol dialkylamine. After stirring for 2 days at RT the mixture was extracted with 2N HCl. The aqueous layer was made basic with 2N NaOH and extracted with $CH_2Cl_2$. The organic layer was dried and evaporated.

EXAMPLE 24

N-(3,4-dihydro-6-methoxy-2,2,7,8-tetramethyl-2H-1-benzopyran-5-yl)-(diethylamino)acetamide Use of N-(3,4-dihydro-6-methoxy-2,2,7,8-tetramethyl-2H-1-benzopyran-yl)-bromoacetamide as employed above afforded 0.29 g (72%) of the desired compound named above. $^1$H NMR δ 8.97 (bs, 1H), 3.59 (s, 3H), 3.19 (s, 2H), 2.66 (q, 6H), 2.59 (t, J=6.7 Hz, 2H), 2.16 (s, 3H), 2.08 (s, 3H), 1.71 (t, J=6.7 Hz, 2H), 1.30 (s, 6H), 1.13 (t, J=7.1 Hz, 6H) $^{13}$C NMR δ 170.7, 148.3, 145.8, 128.0, 125.4, 124.3, 116.6, 73.5, 60.9, 57.7, 48.9, 32.5, 26.9, 19.6, 12.4, 12.3, 11.9

EXAMPLE 25

N-(3,4-dihydro-2-hexyl-6-methoxy-2,7,8-trimethyl-2H-1-benzopyran-5-yl)-(diethylamino)acetamide Use of N-(3,4-dihydro-2-hexyl-6-methoxy-2,7,8-trimethyl-2H-1-benzopyran-yl)-bromoacetamide as employed above afforded 0.36 g (74.5%) of the desired compound named above. $^1$H NMR δ 8.96 (bs, 1H), 3.59 (s, 3H), 3.19 (s, 2H), 2.66 (q, 6H), 2.57–2.50 (m, 2H), 2.16 (s, 3H), 2.07 (s, 3H), 1.8–1.56 (m, 4H), 1.5–1.27 (m, 8H), 1.23 (s, 3H), 1.12 (t, J=7.1 Hz, 6H) 0.86 (t, J=6.5 Hz, 3H) $^{13}$C NMR δ 170.7, 149.0, 145.7, 128.0, 125.4, 124.3, 116.8, 75.5, 60.9, 57.6, 48.8, 40.0, 31.8, 30.8, 29.8, 23.9, 23.6, 22.6, 19.2, 14.1, 12.5, 12.4, 11.8

General Procedure for the Preparation of (3,4-dihydro-6-hydroxy-2,2,7,8-tetraalkyl-2H-1-benzopyran-5-yl)-(dialkylamino)acetamides The deprotection of the methoxy group was carried out following the general procedure of d–e. The amides were purified by column chromatography ($CH_2Cl_2$/MeOH 95:5).

EXAMPLE 26

N-(3,4-dihydro-6-hydroxy-2,2,7,8-tetramethyl-2H-1-benzopyran-5-yl)-(diethylamino)acetamide Use of N-[3,4-dihydro-6-methoxy-2,2,7,8-tetramethyl-2H-1-benzopyran-yl]-bromoacetamide (0.72 mmol) afforded 0.19 g (81%) of the desired compound named above. $^1$H NMR δ 9.5 (bs, 1H), 8.27 (bs, 1H), 3.23 (s, 2H), 2.69 (q, 6H), 2.54 (t, J=6 Hz, 2H), 2.20 (s, 3H), 2.09 (s, 3H), 1.79 (t, J=7 Hz, 2H), 1.23 (s, 6H), 1.09 (t, J=7 Hz, 6H); $^{13}$C NMR δ 171.2, 145.1, 140.8, 126.2, 124.0, 120.4, 109.3, 72.5, 57.4, 48.6, 32.4, 26.5, 19.4, 12.4, 12.3, 11.8 Anal. ($C_{19}H_{30}N_2O_3$) C,H,N.

EXAMPLE 27

N-(3,4-dihydro-2-hexyl-6-hydroxy-2,7,8-trimethyl-2H-1-benzopyran-5-yl)-(diethylamino)acetamide Use of N-(3,4-dihydro-2-hexyl-6-methoxy-2,7,8-trimethyl-2H-1-benzopyran-yl)-bromoacetamide (0.5 mmol) afforded 0.12 g (62%) of the desired compound named above. $^1$H NMR δ 9.5 (bs, 1H), 8.27 (bs, 1H), 3.24 (s, 2H), 2.69 (q, 6H), 2.53 (t, J=6 Hz, 2H), 2.20 (s, 3H), 2.09 (s, 3H), 1.8–1.65 (m, 2H), 1.6–1.26 (m, 10H), 1.21 (s, 3H), 1.09 (t, 6H), 0.86 (t, 3H); $^{13}$C NMR δ 171.2, 145.0, 140.8, 126.2, 124.1, 120.4, 109.5, 73.7, 57.4, 48.6, 39.4, 31.8, 31.0, 29.7, 23.6, 23.5, 22.6, 19.1, 14.0, 12.4, 11.8 Anal. ($C_{24}H_{40}N_2O_3$) C,H,N.

General Procedure for the Preparation of 2,3-dihydro-6-hydroxy-2,2,5,7,8-pentaalkyl-4H-1-benzopyran-4-ones To a solution of 2,4,5-trialkyl-3,6-dihydroxyacetophenone (15 mmol) in 15 mL absolute ethanol was added the appropriate ketone (15 mmol), pyrrolidine (45 mmol) and powdered 3 Å molecular sieves (2.5 g). The resulting mixture was heated at 50–60° C. overnight. The reaction mixture was poured to ice, 10N HCl was added and the mixture was extracted with ether. The organic layer was extracted with sat. aq. NaCl and was dried with anhydrous $Na_2SO_4$. The solvent was evaporated in vacuo and the crude product was purified by flash column chromatography using the appropriate mixture of pet. ether/ethyl acetate as eluting solvent.

EXAMPLE 28

2,3-dihydro-6-hydroxy-2,2,5,7,8-pentamethyl-4H-1-benzopyran-4-one

Use of 2,4,5-trimethyl-3,6-dihydroxyacetophenone and acetone as employed above afforded 1.59 g (38%) of the desired compound named above: $^1$H NMR: δ 11.90 (s, 1H), 2.65 (s, 2H), 2.16 (s, 3H), 2.07 (s, 3H), 2.03 (s, 3H), 1.41 (s, 6H); $^{13}$C NMR: δ 198.17, 156.87, 154.14, 147.62, 115.30, 114.50, 104.96, 77.88, 47.92, 26.65, 16.93, 11.18, 10.53

EXAMPLE 29

2,3-dihydro-2-hexyl-6-hydroxy-2,5,7,8-trimethyl-4H-1-benzopyran-4-one

Use of 2,4,5-trimethyl-3,6-dihydroxyacetophenone and 2-octanone as employed above afforded 3.22 g (62%) of the desired compound named above: $^1$H NMR: δ 11.95 (s, 1H), 2.72, 2.59 (AB q, J=16.88 Hz, 2H), 2.18 (s, 3H), 2.08 (s, 3H), 2.06 (s, 3H), 1.48–1.73 (m, 2H), 1.35 (s, 3H), 1.35–1.16 (b s, 8H), 0.83 (t, J=6.3 Hz, 3H); $^{13}$C NMR: δ 198.63, 157.05, 154.56, 147.90, 115.49, 114.75, 105.43, 80.26, 47.12, 39.56, 31.82, 29.60, 24.10, 23.65, 22.68, 17.24, 14.17, 11.42, 10.81.

General Procedure for the Preparation of 2,3-dihydro-6-hydroxy-2,2,5,7,8-pentaalkyl-4H-1-benzopyran-4-one-oximes To a solution of the appropriate 2,3-dihydro-6-hydroxy-2,2,5,7,8-pentaalkyl-4H-1-benzopyran-4-one (0.77 mmol)

in dry pyridine 5 mL was added hydroxylamine hydrochloride (890 mg, 12.8 mmol) and the resulting mixture was stirred at 70° C. overnight. After cooling the reaction mixture to room temperature the pyridine was evaporated in vacuo and the residue was taken up with ethyl acetate. The organic layer was extracted with water and sat. aq. NaCl and was dried with anhydrous $Na_2SO_4$. The solvent was evaporated in vacuo and the crude product was used without further purification for the next step.

EXAMPLE 30

2,3-dihydro-6-hydroxy-2,2,5,7,8-pentamethyl-4H-1-benzopyran-4-one-oxime

Use of 2,3-dihydro-6-hydroxy-2,2,5,7,8-pentamethyl-4H-1-benzopyran-4-one as employed above afforded 0.224 g (100%) of the desired compound named above: $^1$H NMR: δ 10.97 (s, 1H), 7.50 (b s, 1H), 2.88 (s, 2H), 2.18 (s, 3H), 2.14 (s, 3H), 2.07 (s, 3H), 1.37 (s, 6H); $^{13}$C NMR: δ 155.67, 152.76, 140.14, 124.50, 115.25, 109.80, 100.81, 74.21, 33.71, 26.89, 16.46, 11.47, 11.34.

EXAMPLE 31

2,3-dihydro-2-hexyl-6-hydroxy-2,5,7,8-trimethyl-4H-1-benzopyran-4-one-oxime

Use of 2,3-dihydro-2-hexyl-6-hydroxy-2,5,7,8-trimethyl-4H-1-benzopyran-4-one as employed above afforded 0.278 g (100%) of the desired compound named above: $^1$H NMR: δ 11.10 (s, 1H), 2.87 (s, 2H), 2.18 (s, 3H), 2.14 (s, 3H), 2.07 (s, 3H), 1.52–1.72 (m, 2H), 1.35–1.43 (m, 2H), 1.31 (s, 3H), 1.26 (b s, 6H), 0.86 (t, J=6.4 Hz, 3H); $^{13}$C NMR: δ 155.29, 152.74, 139.84, 124.10, 115.14, 115.042, 109.74, 101.16, 76.29, 39.49, 32.57, 31.74, 29.57, 24.05, 23.55, 22.56, 16.42, 14.05, 11.45, 11.34.

General Procedure for the Preparation of 4-amino-3,4-dihydro-2,2,5,7,8-pentaalkyl-2H-1-benzopyran-6-ols To a solution of $TiCl_4$ (0.17 mL, 1.53 mmol) in dimethoxyethane (2 mL) at 0° C. was added $NaBH_4$ (116 mg, 3.06 mmoles). The mixture was stirred at 0° C. for 10 minutes and subsequently a solution of the appropriate 2,3-dihydro-6-hydroxy-2,2,5,7,8-pentaalkyl-4H-1-benzopyran-4-one-oxime (0.51 mmoles) in 2 ml dimethoxyethane was added dropwise. The mixture was stirred at room temperature overnight. The reaction mixture was cooled to 0° C. and water was added. The mixture because basic with the addition of 28% aqueous ammonia and was extracted with methylene chloride. The organic layer was extracted with sat. aq. NaCl and was dried with anhydrous $Na_2SO_4$ and the solvent was evaporated in vacuo. The product was used as such for the next step.

EXAMPLE 32

4-amino-3,4-dihydro-2,2,5,7,8-pentamethyl-2H-1-benzopyran-6-ol

Use of 2,3-dihydro-6-hydroxy-2,2,5,7,8-pentamethyl-4H-1-benzopyran-4-one-oxime as employed above afforded 74 mg (52%) of the desired compound named above: $^1$H NMR: δ 4.16–4.10 (m, 1H), 2.14 (s, 3H), 2.11 (s, 3H), 2.04 (s, 3H), 2.22–1.99 (m, 2H), 1.38 (s, 3H), 1.19 (s, 3H).

EXAMPLE 33

4-amino-3,4-dihydro-2-hexyl-2,5,7,8-tetramethyl-2H-1-benzopyran-6-ol

Use of 2,3-dihydro-2-hexyl-6-hydroxy-2,5,7,8-trimethyl-4H-1-benzopyran-4-one-oxime as employed above afforded 97 mg (55%) of the desired compound named above: $^1$H NMR: δ 4.20–4.15 (m, 1H), 2.18 (s, 3H), 2.12 (s, 3H), 2.03 (s, 3H), 2.22–2.01 (m, 2H), 1.78–1.15 (m, 13H), 0.85 (t, J=6.4 Hz, 3H).

General Procedure for the Preparation of N-(3,4-dihydro-6-hydroxy-2,2,5,7,8-pentaalkyl-2H-1-benzopyran-4-yl)-bromoacetamides The 4-amino3,4-dihydro-2,2,5,7,8-pentaalkyl-2H-1-benzopyran-6-ol (0.3 mmol) was dissolved in a mixture of tetrahydrofuran/water. To the solution was added $NaHCO_3$ and the appropriate acid chloride dropwise until the starting material had dissappeard. The mixture was taken up in dichloromethane and the organic layer was extracted sequentially with saturated aq. $NaHCO_3$ and saturated aq. NaCl and was dried with anhydrous $Na_2SO_4$ and the solvent was evaporated in vacuo. The product was purified by flash column chromatography using the appropriate mixture of petroleum ether/ethyl acetate as eluent.

EXAMPLE 34

N-(3,4-dihydro-6-hydroxy-2,2,5,7,8-pentamethyl-2H-1-benzopyran-4-yl)-bromoacetamide Use of 4-amino-2,2,5,7,8-pentamethyl-3,4-dihydro-2H-1-benzopyran-6-ol as employed above afforded 0.1 g (82%) of the desired compound named above: $^1$H NMR: δ 6.5 (b s, 1H), 5.15–5.05 (m, 1H), 3.88 (s, 2H), 2.21 (s, 3H), 2.12 (s, 3H), 2.11 (s, 3H), 2.22–1.98 (m, 2H), 1.32 (s, 3H), 1.25 (s, 3H).

EXAMPLE 35

N-(3,4-dihydro-2-hexyl-6-hydroxy-2,5,7,8-tetramethyl-2H-1-benzopyran-4-yl)-bromoacetamide Use of 4-amino-2-hexyl-2,5,7,8-tetramethyl-3,4-dihydro-2H-1-benzopyran-6-ol as employed above afforded 0.110 g (79%) of the desired compound named above: $^1$H NMR: δ 7.12 (bs, 1H), 5.20–5.10 (m, 1H), 3.81 (s, 2H), 2.15 (s, 3H), 2.05 (s, 3H), 2.01 (s, 3H), 2.18–1.99 (m, 2H), 1.75–1.12 (m, 13H), 0.85 (t, J=6.4 Hz, 3H).

General Procedure for the Preparation of N-(3,4-dihydro-6-hydroxy-2,2,5,7,8-pentaalkyl-2H-1-benzopyran-4-yl)-(dialkylamino)acetamide Use of N-(3,4-dihydro-6-hydroxy-2,2,5,7,8-pentaalkyl-2H-1-benzopyran-4-yl)-bromoacetamides as described for the preparation of Examples 24 and 25 affords the desired compounds.

EXAMPLE 36

N-(3,4-dihydro-6-hydroxy-2,2,5,7,8-pentamethyl-2H-1-benzopyran-4-yl)-(diethylamino)acetamide Use of N-(3,4-dihydro-6-hydroxy-2,2,5,7,8-pentamethyl-2H-1-benzopyran-4-yl)-bromoacetamide as employed above afforded 93 mg (95%) of the desired compound named above: $^1$H NMR: δ 8.41 (s, 1H), 8.22 (d, J=8.46 Hz, 1H), 5.17–5.11 (m, 1H), 3.10, 3.05 (AB q, J=17.48 Hz, 2H), 2.52 (q, J=7.04 Hz, 4H), 2.22–2.01 (m, 1H), 2.16 (s, 3H), 2.13 (s, 3H), 2.07 (s, 3H), 1.85–1.80 (m, 1H), 1.45 (s, 3H), 1.39 (s, 3H), 0.97 (t, J=7.05 Hz, 6H); $^{13}$C NMR: δ 173.86, 151.28, 148.88, 136.89, 128.93, 128.13, 115.20, 105.06, 72.37, 56.99, 48.41, 39.92, 39.82, 28.50, 26.92, 16.02, 12.22, 11.85, 11.52

EXAMPLE 37

N-(3,4-dihydro-2-hexyl-6-hydroxy-2,5,7,8-tetramethyl-2H-1-benzopyran-4-yl)-(diethylamino)acetamide Use of N-(3,4-dihydro-2-hexyl-6-hydroxy-2,5,7,8-tetramethyl-2H-1-benzopyran-4-yl)-bromoacetamide as employed above afforded 0.102 g (94%) of the desired compound named above: $^1$H NMR: δ 8.47 (s), 8.22 (d, J=9.1 Hz), 8.11 (s), 8.00 (d, J=9.2 Hz), 5.17–5.13 (m, 1H), 3.09–3.02 (m, 2H), 2.52 (q, J=7.12 Hz, 4H), 2.16 (s, 3H), 2.13 (s, 3H), 2.07 (s, 3H), 2.11–2.02 (m, 1H), 1.92–1.85 (m, 1H), 1.79–1.25 (m, 13H), 0.97 (t, J=7.14 Hz, 6H), 0.85 (t, J=6.7 Hz, 3H); $^{13}$C NMR: δ 174.01, 173.86, 151.27, 151.15, 148.97, 136.91, 136.77, 115.44, 115.21, 115.11, 105.44, 105.27, 75.00, 74.35, 60.33, 57.04, 56.81, 48.57, 48.44, 41.25, 39.93, 39.80, 39.66, 39.50, 38.33, 31.71, 29.71, 29.59, 24.55, 24.34, 23.72, 23.37, 22.56, 16.03, 14.01, 12.27, 12.10, 11.86, 11.53.

As previously mentioned, the compounds of the present invention combine antioxidant and antiarrhythmic activity. They could also be useful for the treatment of a variety of disorders related to free radials and/or arrhythmias. It should be noted that reference herein to treatment extends to prophylaxis as well as the treatment of established diseases.

The antioxidant activity of the new compounds was initially evaluated as set forth below. in vitro lipid peroxidation (Bationi J. P., Fontecave M., Jaouen M., Mansuy D. "Vitamin E derivatives as new potent inhibitors of microsomal lipid peroxidation" Biochem. Biophys. Res. Com. 1991, 174, 1103)

For these experiments, heat-inactivated hepatic microsomal fraction from untreated Fischer rats (200–220 g), corresponding to 0.125 g liver/ml final volume, was used. The incubation mixture contained the microsomal fraction, ascorbic acid (0.2 mM), in Tris buffer (50 mM, pH 7.4) and various concentrations (5 μM–1 mM) of the examined compounds dissolved in DMSO. The lipid peroxidation reaction was initiated with the addition of a freshly prepared FeSO$_4$ solution (10 μM) and aliquots were taken at various time intervals for 45 min. Lipid peroxidation was estimated spectroscopically (535 nm vs. 600 nm) as 2-thiobarbitouric acid (TBA) reactive material. Each experiment was performed at least in triplicate.

The effect of various concentrations of representative compounds of the present invention on lipid peroxidation is shown in Table 1. All the tested compounds demonstrated significant antioxidant activity at the micromolar range. However, there are quantitative differences that appear to be connected with the position of the amide substituent and the length of the side chain.

TABLE 1

| Compound | Concentration μM | % Inhibition |
| --- | --- | --- |
| a | 10 | 96.3 |
| b | 10 | 7.7 |
| b | 50 | 91 |
| c | 200 | 0 |
| c | 400 | 48.6 |
| c | 500 | 93.8 |
| d | 10 | 38.4 |
| d | 50 | 98.1 |
| e | 50 | 87.4 |
| f | 50 | 0 |
| f | 1000 | 100 |
| g | 10 | 100 |
| g | 5 | 72.4 |
| h | 10 | 100 |
| h | 5 | 17.4 |
| i | 50 | 98.6 |
| j | 50 | 96.1 |
| Vitamin E | 10 | 21 |
| Trolox | 10 | 49 |

The evaluation of the antiarrhythmic activity of the compounds set forth above was carried out on isolated heart preparations using the Krebs perfused Langerdorff model (Heisier B. E., Ferrier G. R. "Proarrhythmic actions of flecainide in an isolated tissue model of ischemia and reperfusion" J. Pharmacol. Exp. Ther. 1996, 279, 317). Male Wistar rats, 250–300 g, were anesthetized with pentobarbitone (15 mg/rat=5 mg/100 g body weight) and heparinized (1000 IU)

Hearts were excised and washed in ice cold modified Krebs-Henseleit (KHB) buffer of the following composition in Mm: NaCl 118, KCl 4.7, NaHCO$_3$ 25, KH$_2$PO$_4$ 1.2, MgSO$_4$ 1.4, CaCl$_2$ 2.5, Glucose 11. Hearts were mounted on a Langerdorff apparatus, perfused at a pressure 100 mmHg, at 37° C., with KHB (9 ml/min) for 30–40 min and then the "ischemic" KHB solution was applied for 15 min (this solution is a KH buffer in which the glucose is substituted by Tris HCl. The hearts were then perfused with normal KHB for 30 min. Drugs were present during the last 5 min of ischemia and during reperfusion at the final concentration of 30 or 100 μM.

Electrocardiograms were recorded during equilibration, ischemia and reperfusion.

The most important arrhythmias seem to occur during early reperfusion (Li G-R., Ferrier G. R. "Effects of lidocaine on reperfusion arrhythmias and electrophysiological properties in an isolated ventricular muscle model of ischemia and reperfusion" J. Pharmacol. Exp. Ther. 1991, 257, 997). Table 2 shows the incidence of arrhythmias during the reperfusion period for selected examples.

TABLE 2

Incidence of arrhythmias during the reperfusion period

| Compound | (30 μM) | (100 μM) |
| --- | --- | --- |
| control (no drug present) | 12 ± 4 | |
| a | 7 ± 3.5 | 5 ± 2 |
| g | 8 ± 2.1 | 7 ± 2 |
| h | 6 ± 3 | 6 ± 2.5 |

The invention claimed is:
1. A compound of Formula I

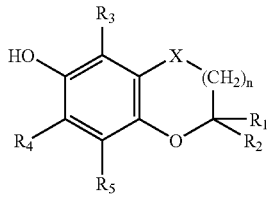

wherein
X=CH$_2$,
n=1,
R$_1$=H, alkyl, alkenyl, alkynyl, aryl all of which may be optionally substituted,
R$_2$=Alkyl, aryl, C(O)Y, C(O)R''', CH$_2$Y(CO)R''', CH$_2$YCH$_2$R''',
R$_3$=Alkyl, C(O)NH(CH$_2$CH$_2$)$_m$NR'R'', NHC(O)CH$_2$NR'R'', NHC(O)R''',
R$_4$, R$_5$=Lower alkyl,
Y=HN(CH$_2$CH$_2$)$_m$NH, HNCHR$_1$NH, HN-cycloalkyl-NH, HN-aryl-NH, heterocyclic diamine, m=1–5
R', R''=Alkyl, and
R'''=(methylsulfonyl)amino-N-aryl.

2. A compound according to claim 1 wherein
X=CH$_2$, n=1,
R$_1$=Me, R$_2$=Alkyl,
R$_3$=CONHCH$_2$CH$_2$NEt$_2$, and
R$_4$, R$_5$=Me.

3. A compound according to claim 1 wherein
X=CH$_2$, n=1,
R$_1$=Me, R$_2$=Alkyl,
R$_3$=NHCOCH$_2$NEt$_2$, and
R$_4$, R$_5$=Me.

4. A compound according to claim 2 wherein the compound is selected from one of the following:
N-(3,4-dihydro-6-hydroxy-2,2,7,8-tetramethyl-2H-1-benzopyran-5-carbonyl)-N',N'-diethyl ethylenediamine;
N-(3,4-dihydro-2-hexyl-6-hydroxy-2,7,8-trimethyl-2H-1-benzopyran-5-carbonyl)-N',N'-diethyl ethylenediamine; and
N-(3,4-dihydro-2-dodecyl-6-hydroxy-2,7,8-trimethyl-2H-1-benzopyran-5-carbonyl)-N',N'-diethyl ethylenediamine.

5. A compound according to claim 3 wherein the compound is selected from one of the following:
N-(3,4-dihydro-6-hydroxy-2,2,7,8-tetramethyl-2H-1-benzopyran-5-yl)-(diethylamino)acetamide; and
N-(3,4-dihydro-6-hydroxy-2-hexyl-2,7,8-trimethyl-2H-1-benzopyran-5-yl)-(diethylamino)acetamide.

6. A process for the manufacture of a medicament for treating and/or reducing reperfusion arrhythmias, said process comprising including in said medicament a compound of Formula I

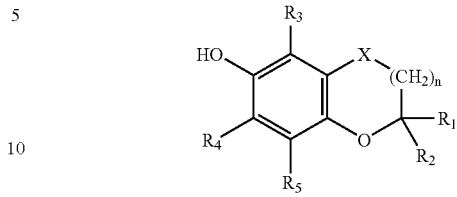

wherein
X=CH$_2$, n=1,
R$_1$=alkyl, alkenyl, alkynyl, or aryl, all of which may be optionally substituted,
R$_2$=Alkyl, aryl, C(O)YC(O)R''', CH$_2$Y(CO)R''', CH$_2$YCH$_2$R''',
R$_3$=Alkyl, C(O)NH(CH$_2$CH$_2$)$_m$NR'R'', NHC(O)CH$_2$NR'R'', NHC(O)R''',
R$_4$, R$_5$=Lower alkyl,
Y=HN(CH$_2$CH$_2$)$_m$NH, HNCHR$_1$NH, HN-cycloalkyl-NH, HN-aryl-NH, heterocyclic diamine, m=1–5,
R', R''=Alkyl, and
R'''=(methylsulfonyl)amino-N-aryl.

7. A pharmaceutical formulation comprising at least one compound of Formula I and/or at least one pharmaceutically acceptable salt thereof

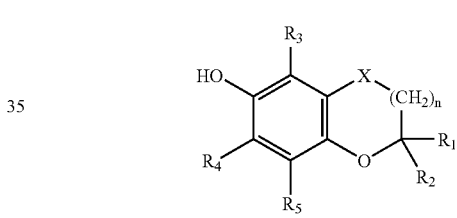

wherein
X=CH$_2$, n=1,
R$_1$=H, alkyl, alkenyl, alkynyl, or aryl, all of which may be optionally substituted,
R$_2$=Alkyl, aryl, C(O)YC(O)R''', CH$_2$Y(CO)R''', CH$_2$YCH$_2$R''',
R$_3$=Alkyl, C(O)NH(CH$_2$CH$_2$)$_m$NR'R'', NHC(O)CH$_2$NR'R'', NHC(O)R''',
R$_4$, R$_5$=Lower alkyl,
Y=HN(CH$_2$CH$_2$)$_m$NH, HNCHR$_1$NH, HN-cycloalkyl-NH, HN-aryl-NH, heterocyclic diamine, m=1–5,
R', R''=Alkyl, and
R'''=(methylsulfonyl)amino-N-aryl.

* * * * *